United States Patent [19]

Moore et al.

[11] 4,231,752

[45] Nov. 4, 1980

[54] METHOD OF DETERMINING SALT WATER IN OILS

[75] Inventors: Edward J. Moore; Michael Sedlak, both of Woodbury, N.J.

[73] Assignee: Mobil Oil Corporation, New York, N.Y.

[21] Appl. No.: 16,247

[22] Filed: Feb. 28, 1979

[51] Int. Cl.$^3$ .................. G01N 33/26; G01N 33/18; G01N 31/02; G01N 33/52

[52] U.S. Cl. .................. 23/230 HC; 23/230 R

[58] Field of Search .................. 23/230 HC, 230 R

[56] References Cited

U.S. PATENT DOCUMENTS

| | | | |
|---|---|---|---|
| 2,968,940 | 1/1961 | Feldman | 23/230 HC X |
| 3,202,483 | 8/1965 | McKeon | 23/230 HC X |
| 3,873,271 | 3/1975 | Young | 23/230 HC |
| 4,089,652 | 5/1978 | Pedersen | 23/230 HC |
| 4,115,063 | 9/1978 | Demers | 23/230 HC |
| 4,151,256 | 4/1979 | Pedersen | 23/230 HC |

*Primary Examiner*—Sidney Marantz
*Attorney, Agent, or Firm*—Charles A. Huggett; Raymond W. Barclay; Claude E. Setliff

[57] ABSTRACT

The presence of salt water in marine oils is determined aboard ship by using a unique combination of reagents comprising a halogenated hydrocarbon, an inorganic salt solution and an alcohol to efficiently separate the water and then using a salt-impregnated gel to determine the chloride content.

10 Claims, No Drawings

METHOD OF DETERMINING SALT WATER IN OILS

BACKGROUND OF THE INVENTION

1. Field of the Invention

The invention relates to a method for determining the nature and amount of salt water held in used oils, especially marine oils. In particular, the method is designed for use on board ship to avoid any delay that is caused when necessary to reach a land-based laboratory for the determination.

2. Discussion of the Prior Art

Various methods have been used to detect the presence of sea water in lubricating oil, particularly marine oils. Generally, such methods are based on the determination of chloride in a sample of the oil. In testing for chlorides by an early method, samples of the used marine lubricating oil were diluted with a suitable light solvent, centrifuged, and the separated water phase at the bottom of the centrifuge tube was removed for chloride analysis. The analysis was carried out by adding silver nitrate to the separated water phase. The formation of insoluble silver chloride in the form of a white precipitate denoted a positive test for the presence of the chloride ion. This test was found to be far from satisfactory in laboratory use, and it was practically unworkable in the field, for example, in marine ports or emergency ports, where laboratory facilities are not available. If, after centrifuging of the lubricating oil, a water phase is not formed, no test can be made for chloride ion, although the oil may actually have chloride contamination. In addition, such tests require, by necessity, a centrifuge and various assorted glassware apparatus, a delicate manipulation to remove water from the centrifuge tube, personal safety considerations in handling of strong acids, relatively easy contamination of chemicals in a marine atmosphere, and the possibility of inaccurate conclusions by reason of the precipitation of organic acids in a manner similar to that of the chlorides.

An improvement to the above-described method is taught in U.S. Pat. No. 3,202,483. In carrying out the chloride determination as described in the patent, a hydrocarbon, water and an emulsion breaker are used to extract the chloride. The chloride containing aqueous solution is then brought into contact with a composite of silver chromate deposited on an absorbent, e.g. silica gel contained in a glass tube. However, the emulsion-breaking action was erratic. Also, the water extract lay below the oil phase so that when the tube containing the silver chromate and absorbent was pushed through the oil phase, the tube picked up oil. Both these difficulties often led to erroneously low chloride values. The present invention relates to an improved system for extracting the chloride.

SUMMARY OF THE INVENTION

In accordance with the invention, there is provided an improved method for determining the presence of salt water in a lubricating oil which comprises the steps of extracting the oil with an aqueous medium and contacting said aqueous medium containing chloride ion with a composite comprising silver chromate deposited on an absorbent, the improvement whereby the aqueous medium used to extract the chloride ion is a combination of aqueous alkali metal or ammonium salt, an aliphatic monohydric alcohol and a halohydrocarbon or mixed halohydrocarbon.

Preferably, the combination comprises aqueous sodium sulfate, 1,1,2-trichlorotrifluoroethane and 1-butanol.

DESCRIPTION OF SPECIFIC EMBODIMENTS

The improved method of the present invention provides a simple, accurate and efficient method of separating water and chloride from oil emulsions, especially marine oil emulsions, so that the chloride in the separated water may subsequently be determined using tubes filled with silver chromate-impregnated silica gel. Thereby the possible contamination of the oil with salt water, e.g., sea-water, may be determined at the source, as for example, onboard ships.

This test is based upon the fact that when the chloride in the oil is transferred to an aqueous medium by an improved combination of reagents, and this aqueous medium is brought into contact with a composite comprising silver chromate deposited on an absorbent, the composite, which normally has a brownish appearance, is changed to a lighter color, varying from a yellowish to a whitish appearance. This color variance results from the formation of relatively insoluble silver chloride from the silver chromate. When this principle is utilized in one of its more practical applications, the quantity of chloride ion present in an aqueous solution can be measured by the relative quantity of silver chromate which is converted to the silver chloride. Thus, when a dry, brown-colored composite of silver chromate deposited on an absorbent, such as silica gel, is packed in a glass tube, an aqueous solution containing chloride ion coming into contact with this composition causes at least a portion of the composite to turn lighter, from a yellowish to a whitish appearance, due to the conversion of the brown silver chromate to the whitish silver chloride. A definite color change is observed, with a sharp line indicating reacted and unreacted silver chromate. The linear length of the reacted portion of the composite (i.e., that portion which has been converted to silver chloride) is proportional to the amount of chloride ion present in the aqueous solution. This length can, therefore, be measured, and to facilitate such measurement, the tube may be suitably calibrated.

When aqueous solutions which are strongly acidic or strongly alkaline are tested by the method of the present invention, the silver chromate in the composite may be dissolved and be converted from the aforementioned brownish color to lighter yellowish or whitish appearance, even though no actual chloride ion is present. On the other hand, where the pH value of the aqueous solution is maintained between about 6 and about 10, the aforementioned color change only occurs when chloride ion is actually present. Therefore, where the aqueous solution to be tested has a pH value outside the aforementioned range, suitable buffering agents may be added to adjust the pH to a value between about 6 and about 10.

While the composite of silver chromate deposited on the absorbent is prepared in such manner that a sufficient quantity of silver chromate is present to react with all of the chloride ion, it varies to a high degree with respect to the quantity of absorbent present in the composite. Thus, composites are generally employed which comprise silver chromate in an amount between 0.25 percent and about 5 percent, and, correspondingly, an absorbent in an amount between about 99.75 percent and about 95 percent, by weight. Composites comprising silver chromate in an amount between about 0.25 percent and about 0.5 percent, and, correspondingly, absorbent in an amount between about 99.75 percent and about 99.5 percent, by weight, are preferred.

The preparation of the composite is carried out by wetting a predetermined amount of the absorbent with an aqueous silver nitrate solution, and then evaporating the absorbent to dryness. The dried absorbent is then reacted with an aqueous solution of sodium chromate and the resulting composite is then evaporated to dryness. The composite is then ready for use in the improved method of the present invention. As a more specific example of the application of the method for preparing the aforementioned silver chromate-absorbent composite, 100 grams of silica gel are wetted with 100 ml. of a 0.02 M aqueous solution of silver nitrate. As indicated above, the silica gel is evaporated to dryness. The dried gel is then contacted with 100 ml. of a 0.03 M aqueous solution of sodium chromate, and the resulting composite is evaporated and ready for use as a chloride ion indicator. In one of the more practical applications of the apparatus suitable for carrying out the improved method of the present invention, a small plug of cotton, or other suitable porous material, is placed in one end of a length of small-bore transparent glass tubing. The dried composite is then packed into the tubing, followed by the insertion of a second plug, so the composite is held firmly in place by the two plugs. Placing an open end of the tube into an aqueous solution containing dissolved chloride ion, will cause the solution to rise up the tube by capillary action, wetting the composite, and affecting the aforementioned color change from a brown to a yellowish or whitish appearance of such linear length of the composite as is proportional to the quantity of chloride ion present in the solution being tested.

While silica gel has been indicated as a suitable absorbent material upon which the silver chromate may be deposited or dispersed, various other materials may also be employed, including silica, silica-alumina, silica-alumina gel, silica-magnesia, glass particles, various vitreous materials, various clays, diatomaceous earth, kieselguhr, pumice, magnesia, alumina-gel, zinc aluminate, zinc alumina, zinc spinel, titania, thoria, zirconia, fuller's earth, "Superfiltrol," sawdust, wood-flour, and any other materials which are capable of absorbing and distributing the silver-chromate in a homogeneous manner. Suitable binders may also be employed in combination with the absorbent material. Preferably, the absorbent employed is a light-colored material to facilitate the observance of subsequent color change in the presence of chloride ion.

As was mentioned hereinabove, the prior art used a hydrocarbon, such as kerosine, an emulsion breaker and water to extract the chloride from the used oil, i.e. marine oil. It is this aspect of the method that the present invention improves. An improved combination of reagents comprising water, a liquid halogenated hydrocarbon that is heavier than water, an alcohol and an inorganic salt is used. The halohydrocarbon or mixed halohydrocarbons may be, among others, trichloroethylene, 1,1,2-trichlorotrifluoroethane, tribromomethane, carbon tetrachloride, o-dichlorobenzene, bromochloroethane, chloroform, dibromopropane, 1,2-dichloroethane, 1-bromonaphthalene and dichloropropane. It should be noted that the effective halohydrocarbons will produce an aqueous medium that will float atop the oil sample, allowing easy contact with such aqueous medium without having to pass the sample probe through the oil layer.

The alcohol may be a liquid monohydroxy alcohol such as 1-butanol, 1-hexanol, propanol, isopropanol, isobutanol, pentyl alcohol or isopentyl alcohol.

The inorganic salt may be one containing a metallic or non-metallic cation and a mono-, or divalent anion. Examples of such cations may be ammonium, or the alkali metal cations. Examples of such anions are fluoride, nitrate, perchlorate and sulfate. Salt anions that cannot be used because they interfere are bromide, iodide, thiocyanate and, of course, chloride.

Effective combinations of reagents in this invention will be in the following ranges. The values are the parts by volume of each reagent required for use with one part by volume of used oil, e.g., marine oil. The 1,1,2-trichlorotrifluoroethane or other halohydrocarbon or combination thereof will range from about 0.7 to about 4.0 parts, preferably about 2.0 parts to about 3.0 parts, the alcohol from about 0.2 to about 1.0 parts, preferably about 0.33 parts to about 0.7 parts, the aqueous solution of inorganic salt from about 0.2 to about 1.0 parts, preferably about 0.33 parts to 0.75 parts. The concentration of the inorganic salt in the aqueous solution will range from about 2% weight to about 12% weight, preferably about 4% to about 8%. The preferred inorganic salt is anhydrous sodium sulfate.

Having described the invention in general terms, the following will illustrate it specifically. It is to be understood that the example below is not intended to limit the scope of the invention.

EXAMPLE

As an example of the method for preparing the aforementioned indicator tubes for chloride ion determination, the composite is first prepared in the following manner:

A silver nitrate solution is prepared by dissolving 3.4 grams of reagent grade silver nitrate ($AgNO_3$) in 50 ml. of distilled water, to which is added an amount of a mixture comprising approximately 90 percent ethyl alcohol and 10 percent methyl alcohol, by volume, sufficient to make one liter of solution. The combined components are then thoroughly mixed. A sodium chromate solution is then prepared by dissolving 4.7 grams of reagent grade sodium chromate ($Na_2CrO_4$) in 100 ml. of distilled water, to which is added an amount of a mixture comprising approximately 90 percent ethyl alcohol and 10 percent methyl alcohol, by volume, sufficient to make one liter of solution. The combined components are thoroughly mixed.

100 grams of silica gel, having a particle size of 100 to 200 mesh, are placed into a 600 ml. beaker. 100 ml. of the aforementioned prepared silver nitrate solution are added and thoroughly mixed with the silica gel. The silica gel must be completely wetted by the silver nitrate solution. If necessary, additional quantities of the aforementioned alcohol mixture may be added to effect complete wetting of the silica gel. The beaker and its contents are then placed on a hot plate and evaporated to complete dryness. To the thus-dried silica gel are added 100 ml. of the aforementioned sodium chromate solution. The components are then thoroughly mixed in the beaker. The beaker is again placed on a hot plate and the contents are evaporated to complete dryness, with occasional stirring to prevent spattering. The last traces of water are removed by placing the beaker in a drying oven maintained at 110° C.

A small plug of cotton is next placed into one end of a glass indicator tube, and the tube is then filled with the dried silver chromate-silica gel composite to a height of 4 inches. Approximately 0.3 gram of the composite is required to fill the tube to the aforementioned height of 4 inches. Thereafter another plug of cotton is inserted into the tube and forced down over the composite so that the latter is retained tightly between the two plugs. The indicator tube is now ready for use.

An extractant mixture was prepared by mixing 5 ml. of an 8% solution of sodium sulfate with 35 ml. of a mixture containing 1 part of n-butanol to each 6 parts of 1,1,2-trichlorotrifluoroethane.

Ten samples of used marine oil from various ships were tested for the presence of sea water. 15 ml. of each of these was shaken with the above extractant mixture for 2 minutes. The mixture was allowed to settle for 1 hour and was then shaken for another two minutes. After further settling the aqueous layer containing the extracted chloride separated and floated above the oil-1,1,2-trichlorotritrifluoroethane-butanol solution. The glass tube containing the silver chromate composite was inserted into the aqueous layer containing the extracted chloride. The aqueous solution rises by capillary action up the tube to the top of the composite, effecting a color change from brown to whitish or yellowish if chloride is present. From the linear length of the yellowish zone and conversion data, Table 1, the sea water content of the oil may be obtained.

TABLE 1

Sea Water Content of Whole Sample vs Height of Indicator Tube Color Change

| Height mm | Grams of Sea Water per 100 g sample | Height mm | Grams of Sea Water per 100 g sample |
|---|---|---|---|
| 5 | 0.03 | 76 | 4.3 |
| 10 | 0.13 | 77 | 4.5 |
| 15 | 0.28 | 78 | 4.8 |
| 20 | 0.43 | 79 | 5.0 |
| 25 | 0.56 | 80 | 5.3 |
| 30 | 0.71 | 81 | 5.5 |
| 35 | 0.86 | 82 | 5.8 |
| 40 | 1.03 | 83 | 6.2 |
| 45 | 1.2 | 84 | 6.5 |
| 50 | 1.5 | 85 | 6.9 |
| 55 | 1.8 | 86 | 7.3 |
| 60 | 2.2 | 87 | 7.8 |
| 62 | 2.4 | 88 | 8.3 |
| 64 | 2.6 | 89 | 8.8 |
| 66 | 2.8 | 90 | 9.4 |
| 68 | 3.0 | 91 | 10.1 |
| 70 | 3.3 | 92 | 10.9 |
| 72 | 3.6 | 93 | 12.0 |
| 74 | 3.9 | 94 | 14.6 |
| 75 | 4.1 | | |

The following Table 2 summarizes the results, which include the times needed for a clear sample of water to settle following the second shaking.

TABLE 2

| Sample | Settling Time Hours | Percent Seawater |
|---|---|---|
| 1 | 6 | 0.62 |
| 2 | 15 | 0.0 |
| 3 | 5 | 0.09 |
| 4 | 4 | 2.4 |
| 5 | 4 | 0.96 |
| 6 | 11 | 1.6 |
| 7 | 11 | 0.40 |
| 8 | 4 | 0.02 |
| 9 | 4 | 0.34 |
| 10 | 6 | 0.16 |

We claim:

1. An improved method for determining the presence of salt water in a lubricating oil which comprises the steps of extracting the oil with an aqueous medium and contacting said aqueous medium containing chloride ion with a composite comprising silver chromate deposited on an adsorbent, the improvement whereby the aqueous medium used to extract the chloride ion is a combination of aqueous alkali metal or ammonium salt, an aliphatic monohydric alcohol and a halohydrocarbon or mixed halohydrocarbons.

2. The method of claim 1 wherein the alkali metal salt is sodium sulfate.

3. The method of claim 1 wherein the halohydrocarbon is 1,1,2-trichlorotrifluoroethane.

4. The method of claim 1 wherein the alcohol is butanol.

5. The method of claim 4 wherein the butanol is 1-butanol.

6. The method of claim 1 wherein the oil is a marine oil.

7. The method of claim 1 wherein the salt is sodium sulfate, the halohydrocarbon is 1,1,2-trichlorotrifluoroethane and the alcohol is 1-butanol.

8. The method of claim 1 wherein the pH of the aqueous medium is maintained at from about 6 to about 10.

9. The method of claim 1 wherein the composite comprises from 0.25 percent by weight to about 5 percent by weight of silver chromate and from about 95 percent by weight to about 99.75 percent by weight of absorbent.

10. The method of claim 1 wherein the aqueous medium is employed to the extent that it comprises per part by volume of oil, (1) from about 0.7 to about 4.0 part by volume of halohydrocarbon, (2) from about 0.2 part to about 1.0 parts per volume of alcohol and from about 0.2 to about 1.0 part by volume of an aqueous salt solution containing from about 2 to about 12 percent by weight of said salt.

* * * * *